US005989221A

United States Patent [19]
Hjertman

[11] Patent Number: 5,989,221
[45] Date of Patent: Nov. 23, 1999

[54] ARRANGEMENT IN ELECTRONICALLY CONTROLLED INJECTION DEVICES

[75] Inventor: Birger Hjertman, Vällingby, Sweden

[73] Assignee: Pharmacia & Upjohn AB, Stockholm, Sweden

[21] Appl. No.: 09/060,052

[22] PCT Filed: Oct. 14, 1996

[86] PCT No.: PCT/SE96/01303

§ 371 Date: Apr. 15, 1998

§ 102(e) Date: Apr. 15, 1998

[87] PCT Pub. No.: WO97/14459

PCT Pub. Date: Apr. 24, 1997

Related U.S. Application Data

[60] Provisional application No. 60/005,773, Oct. 20, 1995.

[30] Foreign Application Priority Data

Oct. 20, 1995 [SE] Sweden .................................. 9503685

[51] Int. Cl.⁶ ................................................. A61M 37/00
[52] U.S. Cl. .......................................................... 604/131
[58] Field of Search .................................... 604/131, 151, 604/152, 154, 141; 128/DIG. 1, DIG. 12, DIG. 13

[56] References Cited

U.S. PATENT DOCUMENTS

| 3,680,558 | 8/1972 | Kapelowitz | 604/89 |
| 4,077,405 | 3/1978 | Haerten et al. | 128/DIG. 12 |
| 4,624,658 | 11/1986 | Mardorf et al. | 128/DIG. 1 |
| 4,695,271 | 9/1987 | Goethel | 128/DIG. 1 |
| 4,950,246 | 8/1990 | Muller | 604/154 |
| 5,254,096 | 10/1993 | Rondelet et al. | 604/152 |
| 5,259,732 | 11/1993 | Stern | 604/154 |
| 5,681,285 | 10/1997 | Ford et al. | 604/151 |

FOREIGN PATENT DOCUMENTS

| 0 285 679 | 4/1987 | European Pat. Off. . |
| 0 293 958 | 5/1988 | European Pat. Off. . |
| 85/02546 | 12/1983 | WIPO . |

OTHER PUBLICATIONS

International Search Report for PCT/SE96/01303.
International-Type Search Report for 9503685-1.

*Primary Examiner*—Jeffrey A. Smith
*Assistant Examiner*—Eduardo C. Robert
*Attorney, Agent, or Firm*—Gilberto M. Villacorta; Pepper Hamilton LLP

[57] ABSTRACT

In an electronically controlled injection device for the administering of one or more injections from an injection cartridge, the readying of the device for administering and the subsequent administering therefrom are controlled by an electronic control unit. This control unit comprises a position or attitude sensor which transmits signals to the control unit such that the readying of the device optionally cannot take place unless the longitudinal axis of the injection cartridge is oriented in a predetermined direction.

21 Claims, 2 Drawing Sheets

ARRANGEMENT IN ELECTRONICALLY CONTROLLED INJECTION DEVICES

RELATED APPLICATIONS

This patent application claims priority from Swedish patent application number 9503685-1, filed Oct. 20, 1995, U.S. provisional patent application No. 60/005,773, filed Oct. 20, 1995, and PCT application number PCT/SE96/01303, filed Oct. 14, 1996 all of which are incorporated herein by reference, including all references cited therein.

FIELD OF THE INVENTION

The present invention relates to electronically controlled injection devices. More specifically, the invention relates to arrangements in electronically controlled injection devices, which facilitate a correct handling of the device when preparing it for the administering of one or more injections.

BACKGROUND OF THE INVENTION

Electronically controlled injection devices have recently been developed and put on the market. Such devices are generally adapted to utilize an injection cartridge with one or more chambers, and comprise an electronic control unit which may be programmed to carry out the necessary operations for the administering of injections.

Examples of electronically controlled injection devices according to the prior art are described in EP-A-0 164 539 and EP-A-0 293 958. These references give a good overview of the state of the art in this field.

Electronically controlled injection devices have turned out to have a number of important advantages, especially in those cases where the patient has to administer the injections to himself, as is the case in the ambulatory treatment of diabetics with insulin. The dose to be administered may be set in advance by the physician, and may even be set at a different value depending on which time of the day the dose is to be administered. The timer will give a signal when it is time for administering a dose, and the programmed electric motor will ensure that the correct amount is administered. Through modern electronical engineering and integrated circuitry, the device may be made small enough to resemble a fountain pen, which can easily be carried in an inside jacket pocket or in a lady's purse.

However, there is still room for improvements in this field. It is desirable to let the operations for the administering comprise the zeroing of a counter and a display before and after the administering, the removal of entrapped air from the cartridge, the metering out of doses of a predetermined magnitude, and the giving of a signal when the cartridge is empty. It may also be desirable to provide a timer to give a signal at the proper time for administering an injection, as well as other functions. The device may often also comprise an electrical motor which, on a signal from the control unit, drives a piston rod for a predetermined distance, such that a predetermined dose is administered. Other functions are also possible. This especially applies to the preparation and readying of the injection device before the first administering is to be carried out from a freshly inserted injection cartridge. These preparation and readying steps include the mixing of components to reconstitute an injectable composition in the cartridge, when a multi-chamber cartridge is used, the removal of entrapped gas from the cartridge, and the zeroing of the counter and/or display unit in the control unit before the first administering. If a multi-chamber cartridge is used, the mixing of components to reconstitute an injectable preparation is also included in the readying steps.

A multi-chamber injection cartridge usually comprises two chambers within a cartridge barrel, which chambers are separated by a front piston. The front chamber contains a solid component of an injectable composition, and is closed at its front end by a closure which may be pierced by an injection needle or cannula. The rear chamber contains a liquid component of an injectable composition and is closed at its rear end by a rear piston. To prepare the cartridge for the administering of an injectable composition, the rear piston is moved forward. Through the essentially incompressible liquid in the rear chamber, the front piston will then also be moved forward, and will at a predetermined position activate a bypass connection, such that the liquid in the rear chamber will be urged over into the front chamber to be mixed with the solid component and form a solution or dispersion to be injected. Multi-chamber injection cartridges comprising more than two chambers are also known.

The design and function of single-chamber and multi-chamber injection cartridges are well-known to those skilled in the art, and need not be described here in more detail.

When an injection device is to be readied for the administering of injections, an injection cartridge is first positioned and secured in a predetermined location in the device, and a piston rod is brought into contact with the rear face of the rear piston. By advancement of the piston rod forward, the cartridge is then readied for administering, as is described in the foregoing, to reconstitute the injectable composition. During the reconstitution step, an injection needle may be inserted through the front end closure of the cartridge, to afford a connection with the outer atmosphere and prevent the build-up of an overpressure in the cartridge, but this is not strictly necessary at this stage of the process.

The reconstitution of the injectable composition must often be carried out under mild conditions, so that sensitive compositions, such as growth hormones, are not unduly decomposed. For this, the cartridge should be held vertically with its front end pointing upward, and the liquid component should be made to flow calmly into the front chamber without any shaking or agitation to aid in the dissolution of the solid component. Other reconstitution positions, such as vertical with the front end pointing downwards or horizontal, may be utilized, depending on e.g. distribution of the solids or by-pass design and location.

Generally when mixing components it may also be desirable to secure wetting of all solids and all wall surfaces or to impose a certain agitation by turning or rotating the device before subsequent steps in the administration scheme.

The next step in the readying of the injection device is the removal of bubbles of air and other gases from the cartridge. This is an important step, even though the amount of enclosed gas in modern injection cartridges is usually not sufficient to cause a health hazard of air embolism if it is accidentally injected. However, as the entrapped gases are compressible, they serve as a buffer, which may give rise to inaccuracies in the metering out of the liquid composition.

The removal of air and other gases is usually carried out in the conventional way: After having inserted an injection needle through the front closure of the cartridge (if this has not been done previously), the user holds the injection device vertically with the needle pointing upward, and advances the piston rod forward until no gas, but only liquid comes out through the needle.

After the gas has been expelled from the cartridge, the metering scale and its display is set at zero or some other desired value before the administering of the injectable composition is started.

In electronically controlled injection devices, the reconstitution of the injectable composition, the removal of enclosed air and the zeroing of the metering scale are usually carried out automatically when the user pushes a start button or the like.

From what has been stated above, it follows that the process of readying an injection device for the administering of injections is a rather delicate process, which demands considerable care from the user. However, this is often forgotten by the user, who usually has no medical training. Thus, the reconstitution of the injectable composition is often carried out with the cartridge in any arbitrary orientation, which may lead to an undesired decomposition of a sensitive composition. The removal of air may be forgotten completely, or may be carried out with the needle pointing in an unsuitable direction, which may lead to an ineffective removal and to spillage of the preparation.

Also during the administration process the device orientation may be critical. Some injection positions may be unsuitable and indicative of improper use. Inadvertent administration of multiple doses may take place unless the device has been moved or turned between two consecutive injections.

Through the present invention, the above shortcomings are eliminated.

SUMMARY OF THE INVENTION

According to the present invention, there is provided an injection device for the administering of one or more injections from an injection cartridge which is arranged in a holder device and at its rear end is provided with a piston which be means of a piston rod may be moved forward, the readying of the device for administering after the positioning of said cartridge-and the subsequent administering therefrom being controlled by an electronic control unit. What characterizes the device is that the control unit comprises a position sensor which emits signals which govern the control unit in such a way that during the readying of the device, forward movement of the piston rod is only made possible when the longitudinal axis of the injection cartridge is oriented in a predetermined direction.

Preferably, this predetermined direction is essentially vertical, with the front end of the cartridge, from which the administering is to take place, pointing upward. However, an essentially vertical direction with the front end of the cartridge pointing downward is also possible.

In a preferred embodiment, the movement of the piston rod is effected by means of an electric motor, which is controlled by the control unit.

In a further preferred embodiment, the injection cartridge is a multi-chamber injection cartridge. The readying of the device for administering one or more injections comprises the reconstitution of an injectable composition and the removal of gases from said composition, and these processes, through the control by the position sensor, are made possible only with the logitudinal axis of the cartridge in an essentially vertical orientation with the front end of the cartridge pointing upward.

DESCRIPTION OF THE PREFERRED EMBODIMENTS

Figure 1:
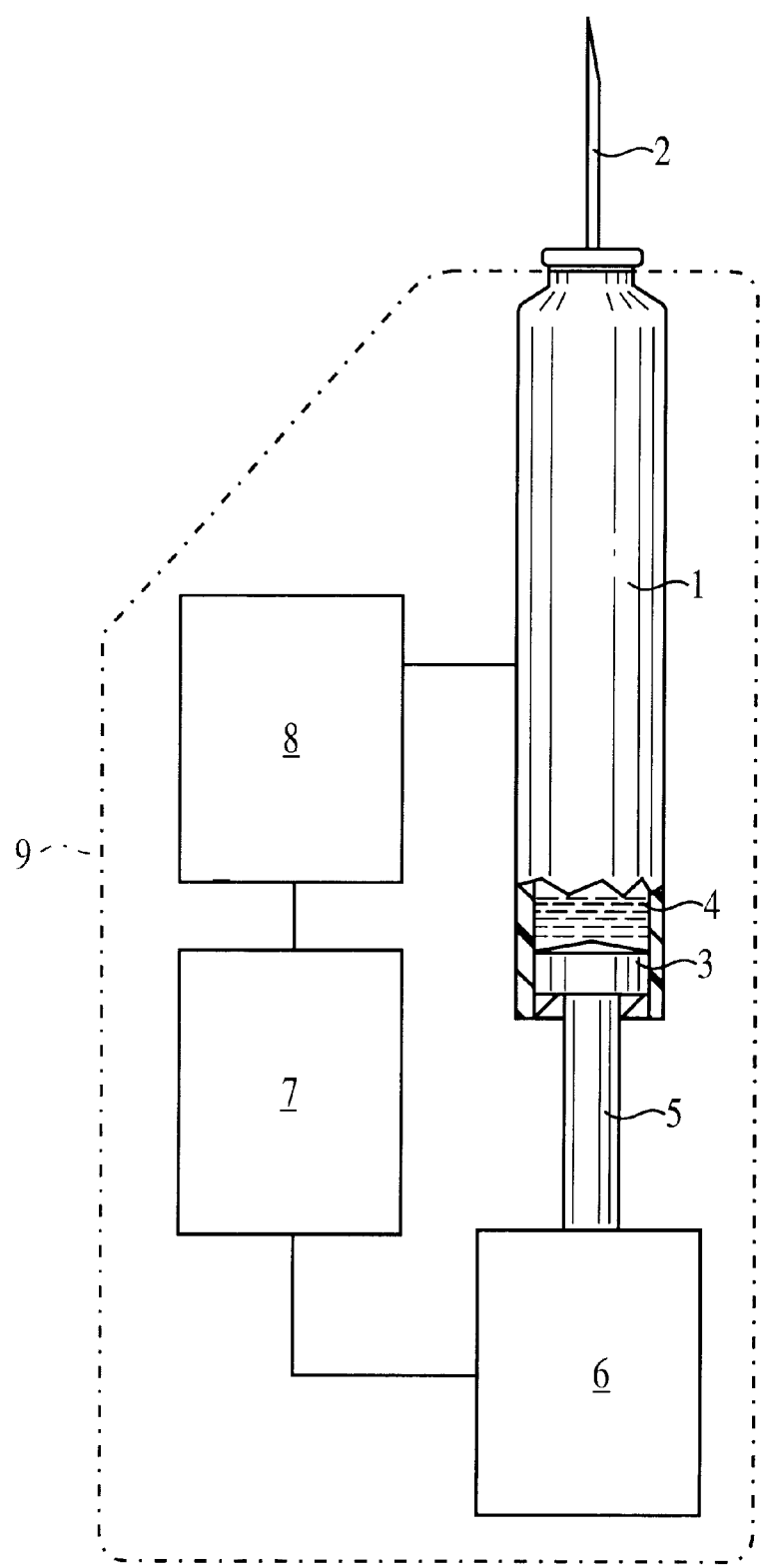
FIG. 1 is a schematic of an embodiment of the instant invention.
Figure 2:
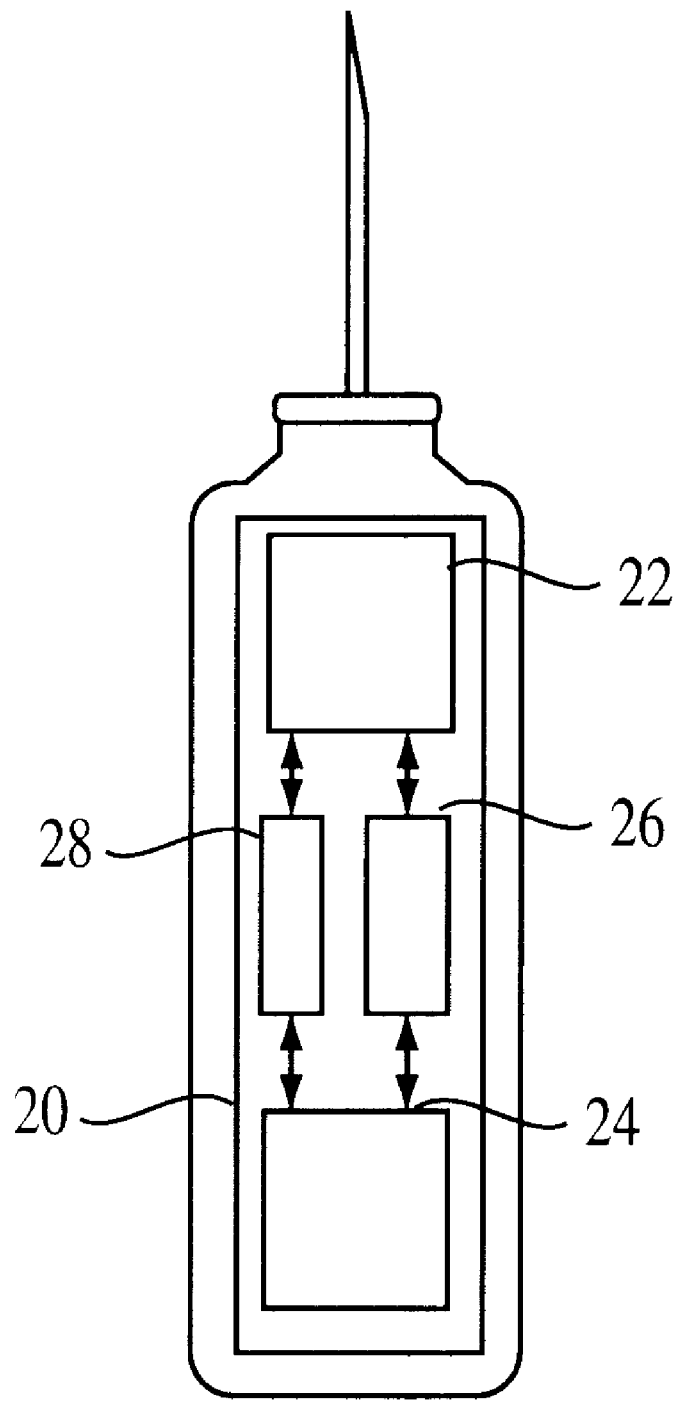
FIG. 2 is a schematic of an alternative embodiment of the instant invention.

In the drawing, the arrangement of the invention is shown schematically. The injection device comprises an injection cartridge 1, which may be of the single. chamber or multichamber type. Preferably, the cartridge is of the dualchamber type. The cartridge is provided with a needle or cannula 2 at its front end and with a rear piston 3 at its rear end. The cartridge contains a liquid component 4, which may fill the cartridge completely in the case of a singlechamber cartridge, or may fill a rear chamber in the case of a multi-chamber cartridge. The rear piston 3 is connected to a piston rod 5, which is actuated by an electric motor 6. The actuation of the motor 6 is governed by signals from the control unit 7. FIG. 2 schematically illustrates an injection device, consistent with the instant invention, including a multi-chamber container or cartridge 20, comprising two or more compartments for components of preparation. The cartridge 20, for example, includes a front chamber or compartment 22, a rear chamber or compartment 24, movable pistons 26 separating the compartments 22 and 24, and a by-pass section 28 for overflow of compartment content.

The position or attitude sensor 8 is mechanically connected to the cartridge 1 in such a way that it senses the orientation of the cartridge 1 and sends corresponding signals to the control unit 7. All the elements of the injection device are arranged in a suitably shaped housing or holder device, which is indicated by the dashed line 9.

The injection device further comprises other elements for fulfilling other functions as desired, such as elements for timing, metering and display. Such elements are known to those skilled in the art, and are not shown in the drawing.

Position or attitude sensors of the type used in the present invention are known and may be of different types. It is also known to incorporate such sensors in an integrated circuit, for instance from the space and missile technology. With knowledge of the present invention, there will be no difficulty for a person skilled in the art to provide a suitable position sensor and install it properly in an electronic injection device.

For example, attitude sensors of this type are available on the market as "Non-Mercury Tip-Over Switches" from PEWATRON AG, Wallisellen/Zurich, Switzerland. These switches are available with different operating angles, i.e. the angle which the switch should be tilted from its vertical axis to switch from a closed to an open circuit. Other types of sensors include the well-known mercury switches. These are less suitable, however, as it is desirable nowadays to get away from the use of mercury as much as possible in all applications, because of its toxic properties.

With reference to the drawing, an example of the function of an injection device of the invention is as follows:

A fresh injection cartridge 1 is placed and secured in a predetermined location in the housing 9, and a needle 2 is inserted through the closure at its front end. The control unit 7 is then actuated to send a signal to the electrical motor 6 to start the readying of the cartridge 1 for the administering of injections.

In a first stage. the piston rod 5 is advanced to get into contact with the rear face of the rear piston 3. The piston 3 will then be urged further forward for the reconstitution of an injectable composition in the cartridge 1, as has been described in the foregoing. When the reconsititution of the composition is complete, the piston rod has been moved forward a given distance, which is sensed by the control unit 7 through signals from the motor 6. The motor usually then stops, as the expulsion of gas from the cartridge does not necessarily have to take place immediately after the reconstitution step.

When air or other gases are to be expelled from the cartridge, the user actuates the motor 6 through the control unit 7. The motor 6 is then kept running and the piston rod 5 is advanced as long as gas is expelled through the needle 2, and the movement of the piston rod 5 is stopped immediately when liquid starts to flow out from the needle 2. All gaseous components should now have been expelled from the cartridge 1.

After the zeroing of a metering scale and/or display (not shown), the device is ready for administering one or more injections. The dose to be injected may be set at this time, or it may already have been programmed into the control unit 7.

During the whole readying process described above, the position or attitude sensor 8 is in mechanical connection with the cartridge 1 and senses its orientation, usually via the housing 9. It is only when the cartridge is in a predetermined orientation, and preferably then an essentially vertical orientation with the needle pointing upward, that the signals from the position sensor 8 will make the control unit 7 send signals to the motor 6 which actuate the motor to move the piston rod 5 forward. Any important deviation from the vertical position will make the position sensor send a signal to the control unit 7 to make it stop the motor 6 and interrupt the readying process. In this way, it is prevented that the readying process takes place with the injection cartridge in an incorrect orientation. The disadvantages mentioned in the foregoing are thereby eliminated.

As stated above, an embodiment is also possible wherein the readying of the device for injection is carried out with the injection cartridge oriented in an essentially vertical direction, but with the front end of the cartridge pointing downward. The front end of the cartridge should be closed. In this embodiment, an overpressure generated when the solution is compressed by means of the piston rod 5 will open a pressure-sensitive valve in the rear piston, such that the air is expelled through the rear end of the cartridge. After the air has been removed from the cartridge, a needle may be attached to the front end of the cartridge, so that an injection may be administered.

After the device has been readied for injection, the control unit 7 will send a signal to the position or attitude sensor 8 such that the sensor is inactivated. This means that the device can now be used in any orientation when injections are to be administered.

The design and assembly of the elements in the device of the present invention is within the competence of a person skilled in the art, once said person has got an understanding of the inventive idea. The various elements are commercially available, or can be manufactured in ways known per se. Also the selection of suitable materials will not pose any great problems to one skilled in the art.

Through the present invention, there has been provided a new arrangement in electronically controlled injection devices, where a number of shortcomings associated with prior art devices have been largely eliminated. This arrangement will make it easier to avoid errors in the handling of electronically controlled injection devices.

It is to be noted that the description of the invention in the present specification and drawings only serves to exemplify the invention, and not to restrict it in any way. Variations and modifications of the embodiments disclosed are possible without departing from the scope of the claims. It is for example not necessary that the signals from the position sensor are used by a control unit for actuation of a motor but they may equally well be used to trigger an alarm or to signal e.g. a warning or instruction message to the operator. Similarly the position switch may not only be used during readying of the device but also during injection for sensing improper positions or proper turning of the device between injections. For the latter purpose the device should include means for registration of a sequence of positions, which is also of value to monitor an agitation step when desired.

I claim:

1. An injection device comprising:
a holder device;
an injection cartridge arranged in the holder device and having a rear end;
a piston provided at the rear end of the injection cartridge and displaceable forwards by a piston rod;
an electronic control unit for at least one of controlling a readying of the device for administering of at least one injection from said injection cartridge after positioning of said injection cartridge and controlling an administering therefrom, said control unit including a position sensor which emits position signals for governing said control unit so that during the readying of the device, forward movement of said piston rod is possible only when a longitudinal axis of said injection cartridge is substantially oriented in a predetermined direction, said control unit deactivating said position sensor or disregarding the position signals therefrom, after the readying of the device.

2. An injection device according to claim 1, further comprising an electric motor, which is controlled by said control unit, effecting movement of said piston rod.

3. An injection device according to claim 1, characterized in that said cartridge is a multi-chamber cartridge and in that said readying also comprises a reconstitution of an injectable composition.

4. An injection device according to claim 3, characterized in that said readying of the device is possible only with the longitudinal axis of the injection cartridge in an essentially vertical orientation, with the front end of the cartridge pointing downwards.

5. An injection device according to claim 3, characterized in that said readying of the device is possible only with the longitudinal axis of the cartridge in an essentially vertical orientation with its front end, from which the administering is to take place, pointing upward.

6. A portable or hand-held injection device comprising a container for a preparation, or components for a preparation, an outlet for the preparation and displacing means at least able to disolace the preparation through the outlet, characterized in that the device further comprises a position sensor designed to emit one or more position signals during readying of the devise indicative of an orientation of the container or component and a control unit designed to receive the position signals and to issue one or more operation signals for the device, the operation signals being at least one of one or more messages and one or more control signals for the displacing means, said control unit deactivating said position sensor or disregarding the position signals therefrom after the readying of the device.

7. The device of claim 6, characterized in that the container may contain gas and that the operation signals are designed to prevent displacing means activation when device orientation is in first predetermined positions unsuitable for deaeration and to allow displacing means activation when device orientation is in second predetermined positions suitable for deaeration.

8. The device of claim 6, characterized in that the container comprises at least two compartments for components of the preparation, that the displacing means are operative to mix contents of at least two compartments and that the operation signals are designed to prevent displacing means activation when device orientation is in first predetermined positions unsuitable for mixing and to allow displacing means activation when device orientation is in second predetermined positions suitable for mixing.

9. The device of claim 8, characterized in that the container is a dual or multi-chamber cartridge with at least one movable piston separating the compartments and a by-pass section for overflow of compartment content past the piston.

10. The device of claim 9, characterized in that the outlet points substantially vertically, in operation.

11. The device of claim 6, characterized in that the control unit is designed to register a change in position sensor signals.

12. The device of claim 11, characterized in that the operation signals are designed to prevent repeated displacing means activation for ejection of preparation through the outlet unless the device has been turned in a predetermined manner between the repeated displacement means activations.

13. The device of claim 11, characterized in that the operation signals are designed to prevent displacing means activation for ejection of preparation through the outlet unless the device has been turned in a predetermined manner.

14. The device of claim 6, characterized in that the operation signals are designed to prevent displacing means activation for ejection of preparation through the outlet when device orientation is in first predetermined positions unsuitable for administration and to allow displacing means activation for ejection of preparation through the outlet when device orientation is in second predetermined positions suitable for administration.

15. The device of claim 6 characterized in that the one or more operation signals are at least one of one or more messages and one or more control signals for the displacing means.

16. The device of claim 15, characterized in that the displacing means incorporates arming means, valve means or fluid control means and that the one or more operation signals are one or more control signals for said arming means, valve means, or fluid control means.

17. The device of claim 15, characterized in that the messages are one or more alarms or instructions detectable by an operator, for guidance of the operator to the actions stated.

18. The device of any one of claims 15, characterized in that the displacing means are activated by actuating means and that the one or more operation signals are one or more control signals for the actuating means.

19. The device of claim 18, characterized in that the actuating means comprises electric motor means for the displacing means.

20. An injection device comprising:

a multi-chamber injection cartridge including a rear piston having a pressure-sensitive gas relief valve;

a position sensor detecting an orientation of a longitudinal axis of said injection cartridge;

a piston rod provided at a rear end of said injection cartridge and communicating with said rear piston, responsive directly or indirectly to said position sensor, wherein said piston rod is displace able forwards during injection readying only when the position sensor detects the orientation to be substantially in a predetermined direction, wherein overpressure generated, prior to injection administration, in said injection cartridge by displacement of said piston rod is reduced via said pressure-sensitive valve.

21. The injection device according to claim 20, further comprising a control unit receiving position signals from said position sensor and controlling said piston rod, said control unit deactivating said position sensor or disregarding the position signals therefrom after the readying of the device.

* * * * *